(12) United States Patent
Mirkov et al.

(10) Patent No.: US 6,479,636 B1
(45) Date of Patent: Nov. 12, 2002

(54) SUGARCANE FRACTIONING SYSTEM

(75) Inventors: T. Erik Mirkov, Harlingen, TX (US); Jean P. Monclin, Lafayette, LA (US); Adam Barrilleaux, New Iberia, LA (US); James E. Irvine, South Padre Island, TX (US); Francis Moonan, Fairfax, VA (US)

(73) Assignees: Honiron Corporation (a Louisiana Corporation), Jeanerette, LA (US); The Texas A&M University (an Agency of the State of Texas), College Station, TX (US)

( * ) Notice: Subject to any disclaimer, the term of this patent is extended or adjusted under 35 U.S.C. 154(b) by 0 days.

(21) Appl. No.: 09/832,321

(22) Filed: Apr. 10, 2001

Related U.S. Application Data

(60) Provisional application No. 60/196,085, filed on Apr. 11, 2000.

(51) Int. Cl.⁷ .............................. C07K 1/34; A01H 5/00
(52) U.S. Cl. ..................... 530/379; 530/414; 530/427; 127/46.2; 127/55; 800/295

(58) Field of Search .................. 800/295; 127/46.2, 127/55; 530/379, 414, 427

(56) References Cited

U.S. PATENT DOCUMENTS

| | | | | |
|---|---|---|---|---|
| 4,359,530 A | * | 11/1982 | Brown | 426/656 |
| 4,627,880 A | * | 12/1986 | Langen et al. | 127/43 |
| 4,963,356 A | * | 10/1990 | Calenoff et al. | 424/276.1 |
| 5,888,789 A | * | 3/1999 | Rodriguez | 435/320.1 |
| 6,372,049 B1 | * | 4/2002 | Shimanskaya et al. | 127/46.2 |

* cited by examiner

*Primary Examiner*—David Brunsman
(74) *Attorney, Agent, or Firm*—Garvey, Smith, Nehrbass & Doody, L.L.C.; Charles C. Garvey, Jr.; Brett A. North

(57) ABSTRACT

A method of extracting and purifying recombinant protein(s) from transgenic sugarcane is disclosed. Fractioning of sugarcane juice that has been extracted from the cane stalks is obtained by using a multiple stage filtering process that uses multiple stages of decreasing porosity (preferably screening) followed by preferably membrane type filters, ion exchange, membrane adsorber, and chromatographic processes.

13 Claims, 1 Drawing Sheet

SUGARCANE FRACTIONING SYSTEM

CROSS-REFERENCE TO RELATED APPLICATIONS

Priority of U.S. Provisional Patent Application Serial No. 60/196,085, filed Apr. 11, 2000, which is incorporated herein by reference, is hereby claimed.

STATEMENT REGARDING FEDERALLY SPONSORED RESEARCH OR DEVELOPMENT

This work was supported by DOD Grant No. DAAG55-97-1-0096. The government may have rights in this invention.

REFERENCE TO A "MICROFICHE APPENDIX"

Not applicable

BACKGROUND OF THE INVENTION

1. Field of the Invention

The present invention relates to the extraction and purification of protein(s), particularly high value proteins, from transgenic sugarcane wherein cane feedstock is fed through a pressure system (eg. mill), filtered with screens, and purified using a combination of membrane filtration, ion exchange and chromatographic processes.

2. General Background of the Invention

Cane sugar is produced from sugarcane stalks in an extraction process that typically involves a grinding of the stalks to produce sugar cane juice. Cane sugar refers to crystalline sucrose, a dissacharide compound used throughout the world as a sweetener. Crystalline sucrose is primarily produced from sugarcane stalks which are cultivated primarily in tropical and semitropical regions of the earth.

In the past, refined cane sugar has been accomplished in primarily two steps. These include the raw sugar process and the refinery process.

In the raw sugar process, sugar mills located in or near cane fields convert the harvested sugarcane stalks into raw sugar. Raw sugar is then refined to produce the white refined sugar that is primarily used for human consumption.

Several patents have issued that are directed sugarcane processing.

U.S. Pat. No. 4,968,353 issued to Kawasaki et al. provides a method for refining sugar liquor. In the '353 patent, a method for refining a sugar liquor by cristobalite and ion exchange resin is provided. Also, a method for refining a sugar liquor by an ion exchange resin refining system are disclosed. Cristobalite exhibits specific adsorbant properties for various colloidal or suspended substances, while the ion exchange resin exhibits superior decoloring and desalting properties with respect to colorants and salts. By combining refining by cristobalite and refining by the ion exchange resin, there is provided a sugar refining system whereby even non-washed sugar liquor may be refined. The ion exchange resin refining system disclosed includes three series of adsorption towers. Each series basically consists of a strongly basic anion exchange resin and a weakly acidic cation exchange resin, and the towers of each of these three series are shifted in a sequence of the pre-stage adsorption tower, the adsorption tower for regeneration, the post-stage adsorption tower and again back to the pre-stage adsorption tower, so that the ability of the strongly basic anion exchange resin may be displayed to the utmost, while the colorant adsorbant properties and the deanionation properties may be exhibited effectively.

In the Gil et al. U.S. Pat. No. 5,281,279 there is disclosed a process for producing refined sugar directly from plants of cane or beet raw juices which bypasses the traditional manufacturing of an intermediate product called "raw sugar". After treatment of the sugar juice with a flocculant, the juice has pressurized air dissolved in it, followed by rapid lowering of the pressure to ambient in a dissolved air flotation cell to separate impurities by aeration. Further amounts of flocculent are added, and the juice is passed through a serpentine flocculator comprising a pipe containing a plurality of relatively straight sections interrupted by sharp bends to expose the juice sequentially to different turbulent regimes defined by different ranges of Reynolds numbers to form flocs containing undissolved solids. Flocs and other undissolved solids are separated from the juice by flotation and settling. The sugar juice or liquor is partially evaporated to a concentration between about 45 degrees and 50 degrees Brix to form a syrup, after which the syrup is again contacted with a flocculent. Following further treatment in the serpentine flocculator and dissolved air flotation cell, the remaining syrup is passed through filters such as silica sand, activated carbon and diatomaceous earth. The filtered syrup is contacted with ion exchange resins to decolorize and deash the syrup, and then it is evaporated to a concentration of 62 degrees–64 degrees Brix. Thereafter sugar is crystallized from the syrup.

The apparatus for separating undissolved impurities by flotation and settling passes sugar liquor between an assembly of closely spaced plates having corrugations in a direction perpendicular to the direction of flow of the liquor. The plates are disposed at an angle so that settled impurities may slide to the bottom of the assembly.

In the Theoleyre et al. U.S. Pat. No. 5,865,899 there is disclosed a process for refining a raw sugar, particularly a raw sugar from the sugarcane industry, characterized by remelting the raw sugar for obtaining a raw sugar syrup, carbonatation or phosphatation of the raw sugar syrup, tangential microfiltration and/or tangential ultrafiltration of the raw sugar syrup. The process is completed by discoloration of the sugar syrup and crystalization and/or demineralization of the sugar syrup.

The Kwok U.S. Pat. No. 5,902,409 discloses a process of manufacturing crystal sugar from an aqueous sugar juice such as cane juice or sugar beet juice.

The Pittet et al. U.S. Pat. No. 6,019,851 discloses a process for producing one or more tastands including food and beverage additives from Saccharum officinarum leaves (sugarcane leaves) by means of carrying out one or more physical separation unit operations in a plurality of such leaves, macerates thereof or mixtures of leaves and macerates thereof, whereby one or more natural food additives is separated and isolated from the remainder of the plurality of leaves, macerates thereof or mixtures of leaves and macerates thereof. Such unit operations include pressurization using hydraulic press means, steam distillation, fractional distillation, supercritical carbon dioxide extraction, volatile solvent extraction and/or charcoal column separation means. Also described is apparatus for carrying out such processes as well as the products produced using such processes and organoleptic uses of such products. Also described are compositions comprising (a) such tastands in admixture with (b) an eatable having a bitter and/or metallic taste. The eatable is any ingested material taken by mammals, such as foodstuffs non-caloric food components or medicines including bitter chocolate or a drug such as ibuprofen.

In the Saska U.S. Pat. No. 6,096,136 there is disclosed the use of nanofiltration to decolorize sugar juice or syrup. The resulting permeate may be used directly to crystalize white sugar without an intermediate step of producing a raw sugar; even though the color of the permeate is substantially higher than the highest color that is acceptable in a conventionally decolorized syrup used to crystalize white sugar. Significant cost savings are thus achieved in producing white sugar.

In the Donovan U.S. Pat. No. 6,174,378 there is disclosed a process for purifying cane juice from an aqueous composition thereof that includes the steps of contacting an aqueous sugar feed composition with sufficient lime to increase the pH of the composition of at least about 9.5; (b) filtering the composition through a membrane having a pore size no greater than about 0.5 microns and having a molecular weight cutoff no less than about 5 kD, thereby producing a retentate and a permeate; and (c) contacting the permeate with sufficient carbon dioxide, or other materials designed to precipitate calcium and lower the pH, to adjust the pH to about 6.5–9.0. The feed composition preferably is cane juice, cane syrup, an aqueous composition of raw sugar, a cane sugar refinery stream, or a mixture of one or more such materials.

Recently, two patents issued to Jean-Pierre Monclin (applicant herein) that relate to the production of raw sugar directly from sugarcane and without using conventional refining processes. In the Monclin U.S. Pat. Nos. 5,468,300 and 5,468,301, clarification of extracted cane juice is obtained by either an ultra-centrifugation or ultra filtration, and removal of certain compounds responsible for adverse color quality and viscosity is effected through a set of packed columns filled with an absorbent for these compounds. After evaporation and crystallization, refined cane sugar is produced.

The following table contains a listing of additional patents that are directed to treating sugarcane, sugarcane juice and/or related processes:

| PATENT NO. | ISSUE DATE | PATENTEE |
|---|---|---|
| 2,610,932 | 09/1952 | EAKIN |
| 2,953,540 | 04/1952 | CORNWELL ET AL. |
| 3,228,876 | 01/1966 | MAHON |
| 3,298,865 | 01/1967 | RODE |
| 3,342,729 | 09/1967 | STRAND |
| 3,781,174 | 12/1973 | NISHIJIMA ET AL. |
| 3,914,410 | 10/1975 | GODFREY |
| 4,039,348 | 08/1977 | HUNWICK |
| 4,083,732 | 04/1978 | PALEY |
| 4,115,147 | 09/1978 | SHIMIZU ET AL. |
| 4,156,618 | 05/1979 | IWAMI ET AL. |
| 4,234,350 | 11/1980 | SUZOR |
| 4,523,959 | 06/1985 | EXERTIER |
| 4,871,397 | 10/1989 | STEVENS |
| 4,950,332 | 08/1990 | STRINGFIELD ET AL. |
| 5,096,500 | 03/1992 | SAN MIGUEL BENTO |

A publication that relates to ultrafiltration and reverse osmosis for cane juice is one of the references cited in the Monclin U.S. Pat. No. 5,468,301. That article is entitled "Application of Ultrafiltration and Reverse Osmosis to Cane Juice", by R. F. Madsen, M.Se., Research Dept., A/S de Danske Sukkerfabrikker, Nakskov, Denmark (pp. 163–167).

The present invention relates to processing of transgenic sugar cane for the recovery (fractional purification) of high value proteins so that these proteins can be separated and further purified from other compounds.

The present invention enables the rapid separation and fractional purification of large quantities of proteins. This process is preferably applied to transgenic sugar cane plant material used to produce essentially any category of recombinant protein(s) such as, but not limited to, monoclonal antibodies (MAB), lectins, collagens, enzymes, or therapeutic proteins. During each step or any of the steps of the process of the present invention, unconventional or conventional laboratory analysis could be performed in order to monitor the streams and the concentration of the protein(s) of interest.

BRIEF SUMMARY OF THE INVENTION

The present invention provides a process for extracting high value protein(s) directly from transgenic sugarcane.

The extraction of transgenic sugarcane feedstock containing the protein(s) of interest can be performed through different means that will not be destructive to the different proteins. Genetically modified and/or non-genetically modified sugarcane plant containing the protein(s) of interest and able to produce a juice when passing through a pressure system can be processed. For example starting with genetically modified sugar cane stalk containing the protein(s) of interest, and passing the stalks through a pressure system such as roller/crusher allows extracting a liquid, in this case also called "pression juice", which contains the protein(s) of interest.

The extracting pressure system can for example use: (a) different geometry rollers, (b) a plurality of rollers, (c) water for further extraction of pression juice, (d) series pressure system where the stalk after the first pressure system will feed a second pressure system in series with the first pressure system, etc. (e) a buffer solution which will avoid partially or entirely, oxidation or degradation of some compounds contained in the pression juice.

In order to improve the juice extraction of the pressure system, the cane stalk can be previously shredded. Both shredder and pressure system are preferably part of the extraction step. The extraction step can work continuously or discontinuously. Extraction could also be performed through a leaching process such as diffusion.

Following the extraction step, the pression juice is transmitted, either by gravity or by means of pumping to a screening system that is preferably composed of one or several screening steps. For example, a three step screening system can be used that is comprised of: (a) a first screening step that removes selected particulate, eg. matter larger than about 500 microns to 1000 microns, (b) the second screening step can be used for removing particulate size larger than about 150 microns to 250 microns, (c) the third screening step can be used to remove particulate size larger than about 10 to 60 microns.

The screening system can include, for example, screens that are stationary, vibrating, rotary or any combination of these types of screens. Screens could also be self-cleaning units. The screened juice is recovered for further processing and the reject is discarded or sent to alternate processing. Press filter(s) or other filtering devices such as pressure filters could be used as an option to the screening step.

The screened juice is transferred to a receiving/mixing tank where its pH is adjusted to a value that is preferably in the range of between about 5.2 to 8.3, accordingly to the protein(s) of interest. The tank could be equipped with a low shear rate-mixing device. The tank is preferably designed to control the temperature of the juice to a value between about 4° Celsius to 70° Celsius.

The juice from the receiving/mixing tank is transmitted (eg. pumped) at constant flow into a first membrane separation system. This first system performs the separation of suspended solids with a size larger than between about 0.1 to 0.2 microns. The clean juice contains the protein(s) of interest. This clean juice or "first permeate fraction" is sent to a receiving tank before transmission to the next method step.

The membrane reject or first retentate fraction is discarded or sent to alternate processing. The first retentate fraction contains contaminants such, as but not limited to: dextrans, waxes, bagacillo, bacterias, yeast, and suspended solids that are typically larger than about 0.1 to 0.2 microns. Membranes can be of different types, materials and configurations. As an example, hollow fiber polymeric membranes can be used. However, composite membranes can be used as well as inorganic (for example, ceramic and coated stainless steel tube membranes) and polymeric membranes with different, selected configurations.

The first membrane separation system can be comprised of a single or several membranes working in parallel or in series. Operating temperature is preferably in the range of between about 4° Celsius to 70° Celsius. Fluxes obtained are preferably in the range of between about 15 to 160 gfd (gallon per square foot per day) at different trans-membrane pressures. During this step some properties of the membrane such as hydrophilicity can enhance the separation process.

The permeate (also called clean fraction from the first step membrane) is collected into a tank called first permeate tank.

The product from the first fraction tank is used to feed at preferably constant flow, the second membrane separation system. This second membrane separation system performs the separation of particulate larger than between about 0.01 to 0.05 microns. The permeate fraction is collected into a tank called the second fraction tank. The retentate fraction is collected into a tank called second retentate tank. According to its (their) molecular size(s), the protein(s) of interest could be in either the second retentate fraction or the second permeate fraction.

Membranes can be of different types, materials and configurations. Hollow fiber polymeric membranes can be used. However, composite membranes can be used as well as inorganic (ceramic and coated stainless steel tube membranes) and polymeric membranes all of them with arrangement including hollow fiber, spiral, plate and tubular module configurations.

The second membrane separation system can be composed of a single or several membranes working in parallel or in series. Operating temperature is preferably in the range of between about 4° Celsius to 70° Celsius. Fluxes can be in the range of between about 5 to 80 gfd (gallon per square foot per day) at different transmembrane pressures. The system can be hydraulically designed in order not to exceed a shear rate of 10,000 $sec^{-1}$. During this step some properties of the membrane such as hydrophilicity can enhance the separation process. The discarded fraction is sent to alternate processing.

The fraction containing the protein(s) of interest, either the second permeate fraction or the second retentate fraction is collected into a second fraction tank. From the second fraction tank, the second fraction is transmitted (eg. pumped) at preferably constant flow into the third membrane separation system, which has cut size of about 5,000 to 80,000 molecular weight.

The membranes used in the third separation system can be made of different material with different shape and configuration. Membranes can be of different types, materials and configurations. The membrane used can be a flat plate configuration, often referred to as "cassettes". However, hollow fiber and spiral wound membranes could also be used. Different materials either regenerated cellulose or polyethersulfone membranes can be used. Other materials that could be used such as polymeric membranes with arrangement including hollow fiber, spiral, plate or tubular module configurations.

The third membrane separation system can be comprised of a single or several membranes working in parallel or in series. Operating temperature is preferably in the range of between about 4° Celsius to 70° Celsius. Fluxes can be in the range of about 0.1 to 30 gfd (gallon per square foot per day) at different transmembrane pressures. The system can be hydraulically designed in order not to exceed a shear rate 10,000 $sec^{-1}$.

The third membrane separation system produces two fractions: (a) the third permeate fraction and (b) the third retentate fraction. The protein(s) of interest is (are) in one of these two fractions. The discarded fraction is sent to alternate processing.

The fraction containing the protein(s) of interest is collected into a third fraction tank prior to any further treatment step during the purification process. The third fraction tank is a receiving/mixing tank where the pH of the fraction is adjusted to a value in the range of between about 5.2 to 8.3, accordingly to the protein(s) of interest. The third fraction tank can be equipped with a low shear rate-mixing device. The third fraction tank can also be temperature controlled to maintain the temperature of the juice to a value between about 4° Celsius to 70° Celsius.

The protein fraction of interest after pH adjustment is transferred (eg pumped) at a rate of about 0.5 to 3.0 beds volume per hour through an ion exchange column containing a weak anionic resin with higher affinity (at this pH of about 4.5 tp 8.3, preferably 5.2 to 8.3) for colorants than any other compounds. Temperature during this step is maintained at a value between about 4° Celsius to 70° Celsius. Decoloration of the incoming feed is between about 25% and 95%.

The decolorized fraction containing the protein(s) of interest is collected into a ion product tank where the pH of the fraction is adjusted to a value in the range of about 5.2 to 8.3, accordingly to the protein(s) of interest. The ion product tank could be equipped with a low shear rate-mixing device. The ion product tank could also be designed to control the temperature of the juice to a value between about 4° Celsius to 70° Celsius. The juice from this ion product tank is transferred (eg. pumped) at a rate of about 0.1 to 3.0 beds volume per hour through an ion exchange chromatographic process for further purification. The ion exchange chromatographic process step produces several fractions, one of them with higher concentration of the protein(s) of interest. A membrane adsorber could replace the ion exchange chromatographic step.

The resulting fraction containing the protein(s) of interest is collected into an ion exchange chromatographic receiving/mixing tank where the pH of the fraction is adjusted to a value in the range of about 5.2 to 8.3, accordingly to the protein(s) of interest. The ion exchange chromatographic tank could be equipped with a low shear rate-mixing device. The ion exchange chromatographic tank could also be temperature controlled to maintain the temperature of the juice to a value between about 4° Celsius to 70° Celsius. The fraction of the protein(s) of interest could be sent to a concentration step such as a low temperature evaporating system for further concentration such as flash/freeze dry. The product from the concentration step (eg. evaporation station) contains the fractionated desired protein(s) partially purified and concentrated.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
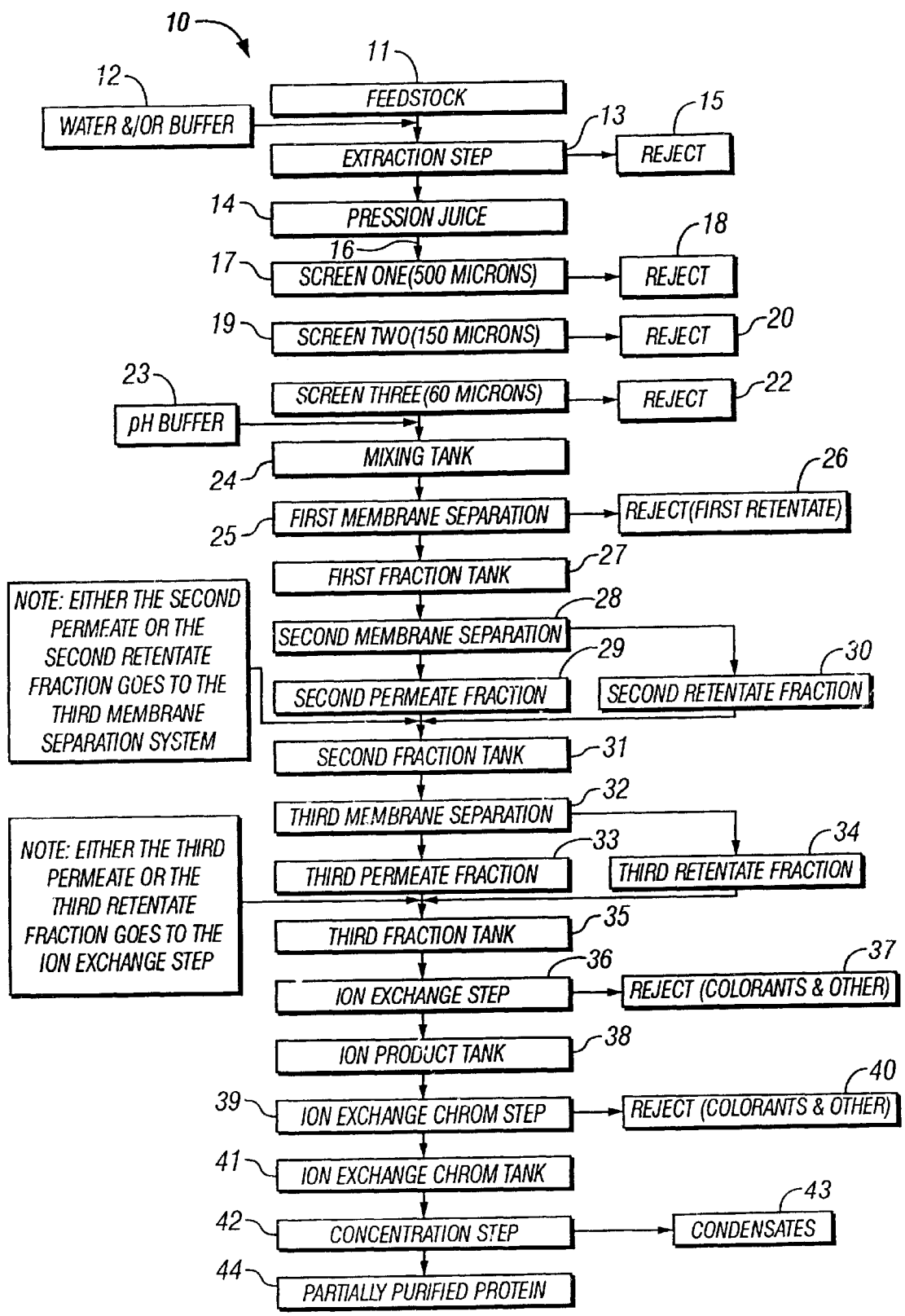
FIG. 1 is a schematic flow diagram illustrating the preferred embodiment of the method and apparatus of the present invention.

FIG. 1 is a schematic diagram of the preferred embodiment of the apparatus of the present invention, designated generally by the numeral 10. FIG. 1 also shows the various method or process steps of the preferred embodiment of the apparatus of the present invention. Sugarcane processing system 10 receives sugarcane feedstock (cane stalks) 11 are treated preliminarily by extraction step 13.

The extraction step 13 can start with genetically modified sugarcane stalks (as the feedstock 11) containing the protein (s) of interest, and passing the stalks through a pressure system such as roller/crusher allows extracting a liquid in this case also called pression juice 14, which contains the protein(s) of interest.

The extracting pressure system or extraction step 13 can use: (a) different geometry rollers, (b) any quantity of rollers, (c) water 12 for further extraction of pression juice 14, (d) series pressure system where the stalks 11 after the first pressure system will feed a second pressure system in series with the first pressure system, etc. (e) a water and/or buffer solution 12 which will avoid partially or entirely oxidation or degradation of some compounds contained in the pression juice 14.

In order to improve the juice extraction of the pressure system, the cane stalks 11 can be previously shredded. Both shredder and pressure system are part of the extraction step 13. The extraction step 13 can work continuously or discontinuously.

Extraction 13 could be also performed through a leaching process such as diffusion.

Following the extraction step 13, the pression juice 16 feeds, either by gravity or by means of pumping to a screening system composed of one or several screening steps 17, 19, 21. For example, a three steps screening system will be composed of: (a) the first screening step 17 could remove particulate matter larger than about 500 microns to 1000 microns, (b) the second screening step 19 used for particulate size larger than about 150 microns to 250 microns, (c) the third screening step 21 removing particulate size larger than about 10 to 60 microns.

Screens 17, 19, 21 could be stationary, vibrating, rotary or any combination of these types of screens. Screens 17, 19, 21 could also be self-cleaning units. The screened juice is recovered at mixing tank 24 for further processing and the reject 18, 20, 22 is discarded or sent to alternate processing.

Press filter(s) or other filtering devices such as pressure filters could be used as an option to the screening step comprised of screens 17, 19, 21.

The screened juice is transmitted to receiving/mixing tank 24 where its pH is adjusted to a value preferably in the range of about 5.2 to 8.3, accordingly to the protein(s) of interest.

The tank 24 can be equipped with a low shear rate-mixing device. The tank 24 can also be temperature controlled to maintain a temperature of the juice to a value about 4° Celsius to 70° Celsius.

The juice from the receiving/mixing tank 24 is transmitted (eg. pumped) at constant flow into a first membrane separation system 25. This first membrane separation system 25 performs the separation of suspended solids with a size larger than about 0.1 to 0.2 microns. The clean juice contains the protein(s) of interest. This clean juice or first permeate fraction is sent to first fraction tank 27 before going into the next step. The membrane reject or first retentate fraction 26 is discarded or sent to alternate processing.

The first retentate fraction 26 contains contaminants such as but not limited to: dextrans, waxes, bagacillo, bacterias, yeast, and suspended solids larger than 0.2 microns. Membranes that are used in system 25 can be of different types, materials and configurations. Hollow fiber polymeric membranes can be used; however, composite membranes can be used as well as inorganic (ceramic and coated stainless steel tube membranes) and polymeric membranes all of them with different configurations. The first membrane separation system 25 can be comprised of a single or several membranes working in parallel or in series. Operating temperature is preferably in the range of about 4° Celsius to 70° Celsius. Fluxes can be in the range of about 15 to 160 gfd (gallon per square foot per day) at different trans-membrane pressure. During this step at first membrane separation system 25 some properties of the membrane such as hydrophilicity can enhance the separation process. As previously indicated, the permeate also called clean fraction from the first step membrane is collected into a tank 27 called first fraction tank.

The product from the first fraction tank 27 is used to feed (at preferably constant flow) the second membrane separation system 28. This system 28 performs the separation of particulate larger than about 0.01 to 0.05 microns. The permeate fraction 29 is collected into a tank called second permeate fraction.

The retentate fraction 30 is collected into a tank called second retentate tank. Accordingly to its (their) molecular size(s), the protein(s) of interest can be either into the second retentate fraction 30 or the second permeate fraction 29. Membranes in the second membrane system 28 can be of different types, materials and configurations. Hollow fiber polymeric membranes can be used: However, composite membranes can be used as well as inorganic (ceramic and coated stainless steel tube membranes) and polymeric membranes all of them with arrangement including hollow fiber, spiral, plate and tubular module configurations. The second membrane separation system 28 can be composed of a single or several membranes working in parallel or in series.

Operating temperature is preferably in the range of a value about 4° Celsius to 70° Celsius. Fluxes can be in the range of about 5 to 80 gfd (gallon per square foot per day) at different transmembrane pressure. The second membrane separation system 28 is hydraulically designed in order not to exceed a shear rate of 10,000 $sec^{-1}$. During this step some properties of the membranes 28 such as hydrophilicity can enhance the separation process. Any discarded fraction can be sent to alternate processing.

The fraction containing the protein(s) of interest can be either the second permeate fraction 29 or the second retentate fraction 30 and is collected into the second fraction tank 31. From the second fraction tank 31, the second fraction is transmitted (eg. pumped) at preferably constant flow into the third membrane separation system 32, which has cut size of about 5,000 to 80,000 molecular weight.

The membrane(s) used in the third separation system 32 can be made of different material with different shape and configuration. Such membranes can be of different types, materials and configurations. The membrane(s) can be flat plate configuration, often referred as cassettes. However, hollow fiber and spiral wound membranes can be used. Different materials such as either regenerated cellulose or polyethersulfone membranes can be used. Other materials can be used such as eg. polymeric membranes with arrangement including hollow fiber, spiral, plate or tubular module configurations.

The third membrane separation system 32 can be comprised of a single or several membranes working in parallel or in series. Operating temperature is in the range of a value about 4° Celsius to 70° Celsius. Fluxes can be in the range of about 0.1 to 30 gfd (gallon per square foot per day) at different transmembrane pressure. The third membrane separation system 32 can be hydraulically designed in order no to exceed a shear rate 10,000 $sec^{-1}$. The third membrane separation system 32 produces two fractions: (a) the third permeate fraction 33 and (b) the third retentate fraction 34. The protein(s) of interest is (are) in one of these two fractions 33, 34. Any discarded fraction can be sent to alternate processing.

The fraction containing the protein(s) of interest is collected into the third fraction tank 35 prior to any further treatment step during the purification process. The third fraction tank 35 is preferably a receiving/mixing tank where the pH of the fraction is adjusted to a value in the range of about 5.2 to 8.3, accordingly to the protein(s) of interest. The tank 35 can be equipped with a low shear rate-mixing device. The tank 35 can also be temperature controlled to maintain the temperature of the processed juice in the tank 35 to a value about 4° Celsius to 70° Celsius. The protein fraction of interest after pH adjustment is transferred (eg. pumped) at a rate of about 0.5 to 3.0 beds volume per hour through an ion exchange column 36 containing a weak anionic resin with higher affinity at this pH of about 5.2 to 8.3 for colorants than any other compounds. Temperature during this step at column 36 is maintained at a value about 4° Celsius to 70° Celsius. Decoloration of the incoming feed is between about 25% and 95%.

The decolorized fraction containing the protein(s) of interest is collected into an ion product receiving/mixing tank 38 where the pH of the fraction is adjusted to a value in the range of about 5.2 to 8.3, accordingly to the protein(s) of interest. The tank 38 can be equipped with a low shear rate-mixing device. The tank 38 can also be temperature controlled to maintain a temperature of the juice to a value about 4° Celsius to 70° Celsius. The juice from tank 38 is transferred (eg. pumped) at a rate of about 0.1 to 3.0 beds per volume through an ion exchange chromatographic process step 39 for further purification. The ion exchange chromatographic process step 39 produces several fractions, one of them with higher concentration of the protein(s) of interest. Membrane adsorber could replace the ion exchange chromatographic step 39.

The resulting fraction containing the protein(s) of interest is collected into an ion exchange chromatographic receiving/mixing tank 41 where the pH of the fraction is adjusted to a value in the range of about 5.2 to 8.3, accordingly to the protein(s) of interest. The tank 41 can be equipped with a low shear rate-mixing device. The tank 41 can also be temperature controlled to maintain a temperature of the juice to a value about 4° Celsius to 70° Celsius. The fraction of the protein(s) of interest could be sent to a low temperature concentration step 42 (eg. evaporating system) for further concentration. Such a concentration step can be, for example, a flash/freeze dry step. The product from the concentration step 42 (evaporation station) contains the fractionated protein(s) 44 partially purified and concentrated.

The following is a list of suitable parts and materials for the various elements of the preferred embodiment of the present invention.

PARTS LIST

| PART NO. | DESCRIPTION |
|---|---|
| 10 | sugarcane fractioning system |
| 11 | sugarcane feedstock |
| 12 | water/buffer |
| 13 | extraction step |
| 14 | pression juice |
| 15 | reject (bagasse) |
| 16 | flowline |
| 17 | first screen |
| 18 | reject |
| 19 | second screen |
| 20 | reject |
| 21 | third screen |
| 22 | reject |
| 23 | ph buffer |
| 24 | mixing tank |
| 25 | first membrane |
| 26 | first retentate fraction |
| 27 | first fraction tank |
| 28 | second membrane |
| 29 | second permeate tank |
| 30 | second retentate fraction |
| 31 | second fraction tank |
| 32 | third membrane |
| 33 | third permeate |
| 34 | third retentate |
| 35 | third fraction tank |
| 36 | ion exchange |
| 37 | rejects |
| 38 | ion product tank |
| 39 | ion exchange chrom |
| 40 | reject |
| 41 | ion exchange chrom tank |
| 42 | concentration step |
| 43 | condensates |
| 44 | partially purified protein |

The foregoing embodiments are presented by way of example only; the scope of the present invention is to be limited only by the following claims.

What is claimed is:

1. A method of refining sugarcane to extract protein matter comprising the steps of:
   a) providing a sugarcane feedstock to be processed;
   b) extracting the sugarcane feedstock to extract cane pression juice;
   c) cleaning the pression sugarcane juice to remove particulate matter;
   d) adjusting the pH of the sugarcane juice to a pH of at least 4.5;
   e) transmitting the juice from steps "a" through "d" to a membrane separation system in order to produce two fractions, one of the fractions containing a protein of interest.

2. The method of claim 1 further comprising the step of removing colorant from the sugarcane juice with ion exchange.

3. The method of claim 1 wherein there is no fermentation involved for the product or separation of protein.

4. The method of claim 1 wherein the screen system has a porosity of between about 60–500 microns.

5. The method of claim 1 wherein the sugarcane juice pH value is adjusted to a range of between about 5.2 and 8.3.

6. The method of claim 1 wherein in step "c" there are at least one filter or multiple screens that include multiple screens having different porosities.

7. The method of claim 1 wherein the membrane separation system of step "e" wherein there are a plurality of membranes.

8. The method of claim 1 wherein there are a plurality of membrane separation stations in step "e" and a plurality of fraction tanks, one fraction tank for each membrane separation station.

9. The method of claim 8 wherein there are at least three membrane separation stations.

10. The method of claim 8 wherein each membrane separation station generates a retentate fraction and a permeate fraction.

11. The method of claim 10 wherein there are a plurality of fraction tanks and each permeate fraction is transmitted to a tank.

12. A process for extraction of protein from sugarcane, comprising the steps of:

a) extracting sugarcane juice from a feedstock of protein contained in sugar cane stalks;

b) preliminarily screening said juice to remove particulate matter, using a plurality of screens spanning a range of porosity of between 50 and 500 microns porosity;

c) treating the cane juice with multiple stages of ultra-clarifying filtration of decreasing porosity, including some ultra-clarifying filtration that includes membrane separation.

13. The process of claim 12 wherein the step of ultra-clarifying the juice comprises ultra-filtering the juice with a membrane having a cutoff that will fractionate proteins having molecular weight between about 5,000 and 500,000.

* * * * *